United States Patent [19]
Drauz et al.

[11] Patent Number: 6,080,887
[45] Date of Patent: Jun. 27, 2000

[54] PROCESS FOR RACEMIZATION OF N-ACETYL-(D)L-α-AMINO CARBOXYLIC ACIDS

[75] Inventors: Karlheinz Drauz, Freigericht; Michael Karrenbauer, Moss-Bankholzen; Andreas Bommarius, Frankfurt; Gunter Knaup, Bruchkobel, all of Germany

[73] Assignee: Degussa Aktiengesellschaft, Frankfurt, Germany

[21] Appl. No.: 09/095,409

[22] Filed: Jun. 10, 1998

Related U.S. Application Data

[63] Continuation-in-part of application No. PCT/EP96/05438, Dec. 5, 1996.

[51] Int. Cl.[7] .................................................. C07B 55/00
[52] U.S. Cl. .......................... 562/401; 562/445; 562/559; 562/575
[58] Field of Search ................................. 562/559, 575, 562/445, 401

[56] References Cited

U.S. PATENT DOCUMENTS 4,602,096  7/1986  Karrenbauer et al. ................... 548/498

FOREIGN PATENT DOCUMENTS 360064952  4/1985  Japan.
361165354  7/1986  Japan.

OTHER PUBLICATIONS

Baxter et al., The Journal of the American Chemical Society, vol. 54, No. 4, pp. 1629–1634, Apr. 1932.

*Primary Examiner*—Gary Geist
*Assistant Examiner*—Rosalynd Keys
*Attorney, Agent, or Firm*—Omri M. Behr, Esq

[57] ABSTRACT

With known methods of racemizing N-acetyl-D(L)-α-amino carboxylic acids in the non-aqueous state by heating them to temperatures above room temperatures, significant quantities of by-products are formed, especially acetyl dipeptides. By converting at least a proportion of the N-acetyl-D(L)-α-amino carboxylic acids to corresponding N-acetyl-D(L)-α-amino carboxylic acid salts before or during the heating, it is possible to increase the sojourn time of the educt which is to be racemized at higher temperatures without any evident increase in the quantity of by-product formed (in particular acetylated dipeptides). Also disclosed is the production of optically active amino acids by enzymatic splitting of racemic compounds.

21 Claims, No Drawings

PROCESS FOR RACEMIZATION OF N-ACETYL-(D)L-α-AMINO CARBOXYLIC ACIDS

RELATED APPLICATIONS

This application is a continuation-in-part of PCT application, PCT/EP96/05438, filed Dec. 5, 1996.

FIELD OF THE INVENTION

This invention is directed to a process for the racemization of N-acetyl-D(L)-α-amino carboxylic acids in a non-aqueous state through heating to higher temperatures than room temperature.

N-acetyl-D(L)-acetyl-α-amino carboxylic acids are precipitated in the form of their salts by the enzymatic hydrolysis of the salts of N-acetyl-D,L-α-amino carboxylic acids with L-amino acid acyclase. They comprise for the most part N-acetyl-D-α-amino carboxylic acids and can also contain smaller amounts of corresponding N-acetyl-L-α-amino carboxylic acids. They can, generally speaking, be racemized after the removal of the L-amino carboxylic acid formed by hydrolysis and again be subjected to enzymatic cleavage.

In the Japanese Patent application JP-A 138603/76, there is disclosed that N-acetyl-D(L)-α-amino carboxylic acid salts in aqueous solution at pH 6–7, can be racemized at a temperature of between 40–90° C. under the addition of at least equal molecular amounts of acidic anhydride.

In this racemation in solution, one unfortunately has to reckon with a non-negligible proportion of by-products. After subsequent concentration by removal of salts, the N-acetylamino acid salts are freed by the addition of mineral acids and the relatively difficulty soluble N-acetylamino acids are precipitated and isolated, a process which in all appears quite complex.

From GB-A 14 17 060, it is already known that N-acetyl-D(L)-α-amino carboxylic acid can be racemized at higher temperatures by heating of their melts. However, in order to achieve a complete racemization, rather long reaction times are required which leads to a substantial discoloration and formation of substantial amounts of dissociation products.

Finally, in DE-A 34 35 095, there is disclosed a further process starting from a melt of N-acetyl-D(L)-α-amino carboxylic acids, in which to the melt relative to the charged N-acetyl-D(L)-α-amino carboxylic acids, there is added from between 0.1 to about 2 wt. % of acetic anhydride and then heated for a time τ (in minutes) to a temperature of between 115–210° C., whereby the melt temperature of the N-acetyl-D(L)-α-amino carboxylic acid forms the lower level of the heating temperature T (in °C.), and the heating temperature and reaction time is described by the equation $$T = \mathrm{Log}_{11} e^{-50\tau+125} + e^{-\frac{5}{3}\tau+155}$$

and the melt, after the reaction time is quenched by the addition of aqueous alkali metal hydroxide or ammonia solution.

Even though the procedures set forth in DE-A 34 35 095 require only a relatively short duration time for complete racemization which are substantially less than the reaction times which are required for the heating of a melt in the absence of acetic anhydride, and thus the discoloration and formation of dissociation products is reduced, nevertheless, in a procedure according to this state of the art, there is still a noticeable formation of by-products, in particular acetyl dipeptides.

In DE-OS 20 44 680, a process is described in which the ammonium salts of an optically active N-acetyl-α-amino phenyl acetic acid are racemized in the presence or absence of water, in that it is heated at temperatures above 150° C. for 10 hours. Since under these conditions ammonia is set free from the salt, this reaction must take place in a sealed tube.

SUMMARY OF THE INVENTION

In view of the state of the art set forth hereinabove, the purpose of the present invention is to provide a process for the racemization of N-Acetyl-D(L)-α-carboxylic acids with higher yields and milder conditions under the substantial avoidance of the formation of by-products.

This task is solved thereby as well as other problems which need not be mentioned, by a procedure for the racemization of N-acetyl-D(L)-α-carboxylic acids in the non-aqueous state by heating at higher temperatures than room temperature. The process comprises heating a composition selected from the group consisting of at least one alkali or alkaline earth salt of said N-acetyl-D(L)-α-amino carboxylic acid and mixtures of said acid with at least one of said salts, in the presence of acetic anhydride of under substantially non-aqueous conditions at temperatures above room temperature, wherein the term D(L)-α-amino carboxylic acid signifies a mixture of the D-isomer of said acid with less than 50 mol % of the L-isomer. Process variants are the subject of the claims dependent on claim 1, whereby either before or during the heat treatment, at least a portion of the N-acetyl-D(L)-α-amino carboxylic acid is converted to the corresponding alkali or alkaline earth salt and heated in the presence of acetic anhydride.

In view of the fact that before or during the temperature treatment, at least a portion of the N-acetyl-D(L)-α-amino carboxylic acid is converted into the corresponding N-acetyl-D(L)-α-amino carboxylic acid salt, it is advantageously a higher temperature and a longer reaction time of the educt to be racemized is made possible without the fear that there would be a raising of the amount of by-products, in particular acetylated dipeptides.

In contrast to the known state of the art with respect to racemization of salts in solution, the use of higher temperatures is made possible which leads to an improvement of the racemization, in particular with respect to reaction speed and yield, while the at least partial neutralization of the educt for racemization, surprisingly leads to a reduction of the by-products.

After the neutralization, in accordance with the prior art, in a timely manner after the racemization (after the reaction period), through quenching with either alkali metal hydroxide or ammonia solution, the change in composition of the mixture to be racemized by the conversion of at least a part of the N-acetyl-amino carboxylic acid into the corresponding salt is responsible in a unforeseeable way for the desirable setting of the conditions of speed of the racemization reaction and by-product production.

In particular, it may be postulated that this may be due to the substantially increased thermal stability of the salts in comparison to the free acetyl amino acids.

In the framework of the invention, the racemization of the N-acetyl-D(L)-α-amino carboxylic acid salts or a mixture of these salts, together with corresponding free acid is carried out in a non-aqueous condition. That is to say, that the racemization is not carried out in aqueous solutions. It should be understood that the absolute absence of water is not a condition of the successful carrying out of the process of the present invention. The level of water should no exceed 5 wt. %, preferably it should be less than <2 wt. %.

Under the conversion of at least a portion of the N-acetyl-D-(L)-amino carboxylic acid into the corresponding N-acetyl-D(L)-α-amino carboxylic acid salts within the scope of the present invention, it should be understood that the racemization can be carried out either in a mixture of free acids and salt or even in the salts itself. The amount of salt present should exceed about 10 mol %.

Insofar as mixture of salt and acid can be utilized for the racemization, the racemization mixture may, for example, be obtained by a mixing the corresponding pure substances.

In a preferred embodiment of the present invention, an aqueous solution of N-acetyl-D-(L)-α-amino carboxylic acid is reacted with a base. Suitably, the base is an alkali or alkaline earth hydroxide, for example, sodium hydroxide, potassium hydroxide, calcium hydroxide, barium hydroxide magnesium hydroxide, or the like, or a carbonate thereof such as sodium carbonate, potassium carbonate, calcium carbonate, or magnesium carbonate. Sodium hydroxide is especially preferred. The amount of base which is added should be such as to hold the pH value below 8.

Suitably, the aqueous solution of N-acetyl-D(L)-α-amino carboxylic acid or a mixture thereof with the corresponding N-acetyl-D(L)-α-amino carboxylic acid salt obtained from the aforesaid treatment with base, should be an aqueous solution having a pH of between about 2 to about 8, preferably between about 4 to about 8, and most particularly between 4.5 to about 5.5.

By the establishment of the particular pH range or value, not only is a substantial amount of the free acid converted to the corresponding salt, but at the same time conditions are set up which are particularly favorable during thermal racemization to provide a satisfactory condition for the desired reaction speed. The setting of the pH value at 2–8, preferably 4–8, most suitably 4.5–5.5 in accordance with the process of the present invention, reduces the danger of hydrolysis of the N-acetyl-D(L)-α-amino acid salt substantially in comparison to that of the free N-acetyl-amino acids and thus also the production by-products, for example, N-acetyl dipeptide, so that even with longer reaction times and higher temperatures, there is virtually no negative influence on the yield. The pH value is most desirably held at 4.5–5.5 since in this pH range the buffering action of the mixture is at a maximum.

In order to achieve the desired pH value, one can utilize virtually any base available to the art in order to form the desired salts of the N-acetyl-D(L)-α-amino carboxylic acids. However, alkaline hydroxide solutions are preferred, in particular those of sodium hydroxide, since the setting of pH levels with aqueous sodium hydroxide is technologically a very simple thing to achieve.

The solution set to the desired pH value by addition of the base in accordance with the present invention, in a useful modification of the process is evaporated to the provision of a dry residue which may be either a solid material or a melt.

It further advantageous when, to the thus obtained residue, whether a melt or a dry material, acetic anhydride is added for racemization by heating.

If the situation is one wherein substance to be racemized is a melt, then the addition of catalytic amounts of acetic anhydride is preferred since the speed of racemization is thus substantially increased.

The melting of an acetyl-D(L)-α-amino carboxylic acid and the heating of the melt is preferably but not essentially carried out under protective conditions, suitably under nitrogen. However, the presence of a protective gas is not essential and the reaction can also be carried in a vacuum.

Even though the use of a melt is highly advantageous for racemization, it has been unexpectedly found that for the successful carrying out of the racemization process of the present invention, it is not absolutely essential to have a melt of the acetyl amino acid salt. In the circumstance where the melting point of the salt in question lies rather high, it is possible to mix the solid substance with appropriate quantities of acetic anhydride and to bring this mixture to a temperature under the melting point of the acetyl amino acid salt. By the addition of the acetic anhydride, a partial melt can be formed and this is adequate for the racemization.

In accordance with the present invention for example, acetyl phenyl alanine sodium and acetyl valine sodium can already be racemized at a temperature of 160° C.

The amount of acetic anhydride to be added within the framework of the present invention is not particularly critical. It is preferred to react a melt or a partial melt under the efficient mixing of between 2–10 wt. %, in particular 2–6 wt. % of acetic anhydride relative to the sum of the weights of the N-acetyl-D(L)-α-amino carboxylic acid and the N-acetyl-D(L)-α-amino carboxylic acid salt.

The temperature at which the racemization should take place should be as high as possible without unnecessarily damaging the substances or causing side reactions to be substantially noticed.

If under these circumstances the provision of a melt is possible so then the melt is heated to and maintained at a temperature which about 5–10° C. above the melting point of the appropriate N-acetyl-D(L)-α-amino carboxylic acid or the salt corresponding thereto, whichever temperature is higher.

If on the basis of the compounds taking part, attaining a complete melt is not possible, it is also advantageous to carry out the racemization in a temperature range of between 100–220° C., suitably in the range of 130–180° C. These ranges, generally speaking, are adequate for all the needs of the process.

For the further work-up of the racemate one may employ any of the generally known procedure or embodiment. It is particularly advantageous if the melt or the partial melt after ending of the heating is taken up in water and then further worked up. The racemization procedure of the present invention may be particularly employed upon the N-acetylated derivatives thereof. For the particularly successful racemization, there may be employed the N-acetyl derivatives of Formula I

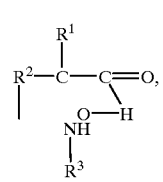

wherein
R$^1$ is hydrogen or C$_{1-4}$ alkyl,
R$^2$ is hydrogen, alkyl, substituted alkyl, aryl, substituted aryl, heteroaryl, aralalkyl, heteroaralalkyl, cycloalkyl, or cycloalkylalkyl, wherein the named residues of themselves may either be substituted and/or contained heteroatoms therein, or $R^1$ and $R^2$ taken together with the carbon atom to which they are attached may be formed into a 3–7 membered saturated ring, $R^3$ may be hydrogen or $C_{1-4}$ alkyl, or $R^2$ and $R^3$ when taken together with the nitrogen and the carbon atom to which they are attached, may form a 4–7 membered saturated ring which may contain a heteroatom.

With respect to $R^2$, the alkyl groups may be straight or branch chained and suitably have a chain length of $C_1$–$C_{12}$ for the straight chains and $C_3$–$C_{12}$ with the branch chains, particularly preferred are chain lengths of $C_1$–$C_6$ for straight chains and $C_3$–$C_6$ with branch chains. As illustrations but not as limitations, there may be cited methyl, ethyl, propyl, isopropyl, butyl, isooctyl and dodecyl.

The aforementioned alkyl groups may be substituted by 1–3 amino groups, hydroxyl, halo, guanidino, ureiodo, carboxy, carboxamido and/or alkoxy groups wherein, the alkyl moiety thereof is as set forth above.

Aryl is suitably phenyl or substituted phenyl wherein the substituent groups are as set forth above with respect to alkyl.

Substituted aryl groups are suitably mono-, di-, or trihalo, mono-, di-, or trihydroxy, mono-, di- or trialkyl phenyl groups, wherein suitably halogen is fluoro, chloro or bromo and alkyl is $C_1$–$C_4$ alkyl, suitably methyl or ethyl.

As heteroalkyl groups there are preferred 5 or 6 ring systems with 1–2 heteroatoms in the ring, suitably oxygen, nitrogen, or sulfur.

As an aralkyl group, benzyl is preferred and cycloalkyl and cycloalkyl methyl, suitably $C_{3-7}$ ring systems.

Especially preferred as compounds falling within the above group are alanine, valine, leucine, isoleucine, proline, tryptophan, phenylalanine, methionine, serine, tyrosine, threonine, cysteine, asparagine, glutamine, histidine, cystine, citrulline, homocysteine, homoserine, hydroxyproline, ornithine and norvaline, as well as the derivatives of the foregoing amino acids, suitably lower alkyl derivatives. Particularly preferred are N-acetyl-D(L)-methionine, -valine, -phenylalanine, and/or norvaline.

Particularly preferred are to be racemized is N-acetyl-D(L)-methionine. In this case, it is preferred to provide a melt by the evaporation of a solution which contains N-acetyl-D(L)-methionine which had previously been prepared by addition of a sufficient amount of aqueous sodium hydroxide to provide a pH value of between 4 and 8, which is then heated to a temperature of between 110–180° C., preferably 150–160° C. under efficient mixing with at least 2 and not more than 6 wt. % of acetic anhydride for a reaction time of from 2–30 minutes, suitably 10–15 minutes, whereafter it is taken up in water.

The present invention is particularly suitable for the racemization of N-acetyl-D(L) amino acids regardless of what source. The racemization therefore is process which is excellently suitable for integration with a procedure for obtaining optically active α-amino acids.

Such an integrated procedure may be characterized, for example for obtaining of L-methionine that the N-acetyl-D(L)-methionine containing solution is a mother liquor and the racemized melt taken up in the water is a recycling solution which may be used in a procedure for obtaining optically active L-methionine, wherein the D,L-methionine is first acylated with acetic anhydride in acetic acid, the thus obtained N-acetyl-D,L-methionine-racemate is enzymatically split, the L-methionine is separated under retention of a mother liquor and the unchanged N-acetyl-D(L)-methionine in the mother liquor after racemization is recycled as a recycling solution for the enzymatic racemate splitting.

The N-acetyl-D(L)-methionine sodium salt and N-acetyl-D(L)-methionine which are charged to the process of the present invention can suitably be obtained in that the mother liquor obtained after the enzymatic hydrolysis following isolation of L-methionine is passed over a strongly acidic cation exchanger which absorbs the thus obtained cations and the remaining L-α-amino carboxylic acid. The solution exiting from the ion exchanger comprises virtually only water, acetic acid and N-acetyl-D(L)-methionine. It is then evaporated under preserving conditions suitably at low temperatures in a vacuum, for example, in a combination of a fallfilm evaporator and a thin layer evaporator with solid removal for the removal of the enzymatic reaction inhibiting acetic acid, and then transferred into aqueous sodium hydroxide at pH 4–8, suitably 4.5–5.5. Alternatively however, the sodium hydroxide may be added prior to the removal of the acetic acid. In the manner, the pH value is already raised before the evaporation whereby the hydrolysis in the chosen example of N-acetyl-D(L) methionine can be reduced.

Even the reaction time for the melting of the N-acetyl-D(L)-α-amino carboxylic acid may be advantageously held as short as possible. The melting is carried in a heated extruder so that the complete melting can generally speaking take place in a duration of less than a minute. In this case, the extruder can move the melt in a heated reaction tube where at the beginning of the reaction path, an appropriately provided pump can continually dose acetic anhydride to the mass over a mixing system.

The invention may be further illustrated by the following Examples. unless otherwise state, all percentages given are percentages by weight.

The charged N-acetyl-D(L)-α-amino carboxylic acid and the racemized samples are examined with respect to their specific rotation $[\alpha]_D^{20}$ in degrees. cm$^3$/dm. grams.

EXAMPLE 1

Racemization of N-Acetyl-D(L)methionine Sodium in a Melt

Experiment 1

10 g. (0.053 mol) N-acetyl-D(L) methionine were taken up in 25 ml. of 8 wt. % sodium hydroxide to a pH of 5 and evaporated to a melt in vacuo at 50 mbar. Subsequently, 0.2 g. of acetic anhydride were stirred in at a temperature of 155° C. These melts were then held at 155° C. for 30 minutes and subsequently taken up in water.

$[\alpha]_D^{20}$ before racemization: +21.3° (c=4 in water)

$[\alpha]_D^{20}$ after racemization: ±0° (c=4 in water)

Content of dipeptide after successful racemization: 0.3 wt. % with respect to N-acetyl methionine.

Experiment 2

Experiment 1 was repeated with a difference that there was utilized about 20 ml. of 8 wt. % sodium hydroxide to a pH value of 4.

$[\alpha]_D^{20}$ after racemization: +0.2° (c=4 in water)

Content of dipeptide after successful racemization: 0.8 wt. % with respect to N-acetyl methionine.

Experiment 3

Experiment 1 was again repeated with the difference that there was utilized 26 ml. of 8 wt. % sodium hydroxide to a pH value of 6.

$[\alpha]_D^{20}$ after racemization: ±0° (c=4 in water)

Content of dipeptide after successful racemization: 0.2 wt. % with respect to N-acetyl methionine.

Experiment 4

Experiment 1 was again repeated with the difference that the melt was treated at a temperature of 1.10–120° C. under the addition of 0.3 g. of acetic anhydride.

$[\alpha]_D^{20}$ after racemization: +0.5° (c=4 in water)
Content of dipeptide after successful racemization: 0.5 wt. % with respect to methionine.

Experiment 5

Experiment 1 was repeated with the difference that the melt temperatures were raised to 180° C. and the reaction time was set to 10 minutes.

$[\alpha]_D^{20}$ after racemization: 0° (c=4 in water)
Content of dipeptide after successful racemization: 0.1 wt. % with respect to N-acetyl methionine.

Experiment 6

Experiment 5 was repeated with the difference that the reaction time was raised to 30 minutes.

$[\alpha]_D^{20}$ after racemization: ±0° (c=4 in water)
Content of dipeptide after racemization: 0.8 wt. % with respect to N-acetyl methionine.

Experiment 7

Experiment 1 was repeated with the difference that there was added about 27 ml of 8 wt. % sodium hydroxide solution to a pH of 8 and 0.3 g. of acetic anhydride is added.

$[\alpha]_D^{20}$ after racemization: ±0° (c=4 in water)
Content of dipeptide after racemization: 0.4 wt. % with respect to N-acetyl methionine.

Experiment 8

Experiment 1 was again repeated with the difference that 0.6 g. of acetic anhydride were added.

$[\alpha]_D^{20}$ after racemization: ±0° (c=4 in water)
Content of dipeptide after racemization: 0.5 wt. % with respect to N-acetyl methionine.

Comparison Experiment 9

Experiment 1 was repeated without the addition of sodium hydroxide (pH ca. 1.6), that is to say free N-acetyl-D(L) methionine was thermally racemized in that the heating time of the melt after addition of the acetic anhydride was set for 155° C. for 30 minutes.

$[\alpha]_D^{20}$ after racemization: ±0° (c=4 in water)
Content of dipeptide after racemization: 5.5 wt. % with respect to N-acetyl methionyl methionine.

The results of the foregoing experiments may be set forth in the following table:

TABLE 1

| Expt/Comp.-Expt | pH-Value | Ac₂O | Temp. | Duration | $[\alpha]_D^{20}$ | Ac-Met-Met |
|---|---|---|---|---|---|---|
| 1 | 5 | 2% | 155° C. | 30 min | 0 | 0.3% |
| 2 | 4 | 2% | 155° C. | 30 min | +0.2 | 0.8% |
| 3 | 6 | 2% | 155° C. | 30 min | 0 | 0.2% |
| 4 | 5 | 3% | 110–20° C. | 30 min | +0.5 | 0.05% |
| 5 | 5 | 2% | 180° C. | 10 min | 0 | 0.1% |
| 6 | 5 | 2% | 180° C. | 30 min | 0 | 0.8% |
| 7 | 8 | 3% | 155° C. | 30 min | 0 | 0.4% |
| 8 | 5 | 6% | 155° C. | 30 min | 0 | 0.5% |
| 9 | 1.6 | 2% | 155° C. | 30 min | 0 | 5.5% |

EXAMPLE 2

Racemization of N-Acetyl-L-Phenyl Alanine Sodium Salt

Vacuum dried samples of N-acetyl-L-phenyl alanine sodium salt were mixed with acetic anhydride and warmed (at 150°). In order to determine the degree of racemization. The specific rotation was measured $[\alpha]_D^{20}$, c=1 in 1N HCl). Before racemization there was specific rotation of +21.6. The results are set forth in the following table:

TABLE 2

| Ac₂O | Temp. | Duration | $[\alpha]_D^{20}$ |
|---|---|---|---|
| 2% | 140° C. | 15 min | 9.0 |
| 2% | 160° C. | 15 min | 2.9 |
| 2% | 180° C. | 15 min | 1.9 |
| 5% | 160° C. | 15 min | 0 |
| – | 230° C. | 15 min | 10.8 |

EXAMPLE 3

Racemization of N-Acetyl-L-Valine Sodium Salt

A sample of N-acetyl-L-valine sodium salt vacuum dried at 150° C. is mixed with acetic anhydride and warmed. For following the racemization the specific rotation $[\alpha]_D^{20}$, c=1 in 1N HCl was determined. Before the racemization, this had a specific rotation value of +11.9. The results are set forth in the following table:

TABLE 3

| Ac₂O | Temp. | Duration | $[\alpha]_D^{20}$ |
|---|---|---|---|
| 2% | 140° C. | 15 min | 10.2 |
| 2% | 160° C. | 15 min | 6.5 |
| 2% | 180° C. | 15 min | 4.8 |
| 5% | 160° C. | 15 min | 1.6 |
| 5% | 230° C. | 15 min | 0 |
| – | 230° C. | 15 min | 8.3 |

EXAMPLE 4

Recycling of an N-Acetyl-D-(L)-Methionine Sodium Salt Mother Liquor 717 g. (23.75 mol) N-acetyl-D,L-methionine and 140 g. (3.50 mol) of sodium hydroxide were dissolved in water and brought to 1.5 l. The pH value of the solution was brought to 7 by the addition of 50% aqueous solution of sodium hydroxide. After the addition of 3.6 g. acylase (activity 31.000 E/g), the mixture was stirred at room temperature for 5 days. The suspension was then cooled to 5° C. The precipitate filtered off and washed with ice water and dried. One thus obtains 174 g. (1.17 mol) of L-methionine. The filtrate (1800 g), which, besides 21.8 wt. % N-acetyl-D(L)-methionine, contains 2.8 wt. % of L-methionine was warmed to 60° C. and reacted with 60 g (0.60 mols) of acetic anhydride. After 30 minutes, no methionine was detected in the solution. 223 g (1.17 mol) of N-acetyl-D,L-methionine were added and concentrated under vacuum to 1200 g. The solution was further concentrated in a Sambay evaporator at 170° C. and 10 m bar to 754 g. Into the still warm melt were added 15 g of acetic anhydride, heated for 10 minutes 140° C. and then dissolved in water and brought up to 1.5 l. The specific rotation of the solution was 0. The content of N-acetyl dipeptide was 0.8% with respect to N-acetyl methionine. After the pH value was adjusted to 7 with sodium hydroxide, this solution was again reacted with the acylase for acylase splitting to yield L-methionine 166 g (1.11 mol).

EXAMPLE 5

Recycling of N-Acetyl-D(L)-Norvaline Sodium Salt mother liquor 597 g. (2.75 mol) of N-acetyl-D,L-norvaline and 140 g (3.50 mol) of sodium hydroxide were dissolved in water and brought to 1.5 l. The pH of the solution was brought to 7 with 50% sodium hydroxide. After addition of 3.0 g of acylase (activity 31.000 E/g) the mixture was stirred at room temperature for 5 days. The suspension was cooled to 5° C., the precipitate filtered off and washed with 300 ml of ice water and dried. One thus obtains 157 g (1.34 mol) of L-norvaline. The filtrate (1393 g), which contains besides 22.5 wt. % N-acetyl-D(L)-norvaline, 3.1 wt. % of L-norvaline is warmed to 60° C. and treated with 64 g (0.62 mol) acetic anhydride. After 30 minutes no norvaline was detectable in the solution. 213 g (1.34 mol) N-acetyl-D,L-norvaline were added and concentrated in vacuo to 950 g. This solution was then further concentrated in a Sambay evaporator to 170° C. and 10 mbar to 644 g. Into this warm melt were added 13 g of acetic anhydride, the mixture heated for 10 minutes to 140° C. and then dissolved in water and brought to 1.5 l. A chromatographic ee-determination showed a D/L ratio of 51.3% to 48.7%. The content of N-acetyl dipeptide was 1.2% with respect to norvaline. After pH value was brought to 7, this solution was subjected to acylase splitting as described above; the yield was 113 g. (0.97 mol) of L-norvaline.

Further modifications and advantages of the invention are set forth in the following claims.

What is claimed is:

1. A process for the racemization of an N-acetyl-D(L)-α-amino carboxylic acid to yield the corresponding N-acetyl-D,L-α-amino carboxylic acid which comprises heating a composition selected from the group consisting of at least one alkali or alkaline earth salt of said N-acetyl-D(L)-α-amino carboxylic acid and mixtures of said N-acetyl-D(L)-α-amino carboxylic acid with at least one alkali or alkaline earth salt of said N-acetyl-D(L)-α-amino carboxylic acid, in the presence of acetic anhydride of under substantially non-aqueous conditions at temperatures above room temperature, wherein the term D(L)-α-amino carboxylic acid signifies a mixture of the D-isomer of said acid with less than 50 mol % of the L-isomer.

2. The process of claim 1 when the water content of the mixture to be heated is less than 5 wt %.

3. The process of claim 1 wherein the heating is carried out at a temperature of between 100 and 220° C.

4. The process of claim 1 wherein there is present at least 10 mol % of one of said salts.

5. The process of claim 1 wherein the amount of acetic anhydride is between 2 and 10 wt %.

6. The process of claim 1 wherein the composition to be racemized is, prior to addition of the acetic anhydride in solid form.

7. The process of claim 1 wherein the composition to be racemized is, prior to addition of the acetic anhydride, in melt form at the temperature of heating.

8. The process of claim 1, which comprises the steps of treating an aqueous solution of the N-acetyl-D(L)-α-amino carboxylic acid or a mixture of an aqueous solution of the N-acetyl-D(L)-α-amino carboxylic acid with a corresponding N-acetyl-D(L)-α-amino carboxylic acid salt, with a base, to bring the pH thereof to a value of 2–8, and then bringing thus obtained solution to dryness or melt prior to racemization.

9. The process of claim 8 wherein the pH is adjusted to a range of 4–8.

10. The process of claim 8 wherein the pH is adjusted to a range of 4.5–5.5.

11. The process of claim 8, which comprises utilizing sodium hydroxide for the pH adjustment.

12. The process of claim 1 wherein the composition to be racemized is in the form of a dry solid which comprises adding thereto a sufficient amount of acetic anhydride to yield a partial melt.

13. The process of claim 1 wherein the composition to be racemized is in the form of a dry solid which comprises adding thereto a sufficient amount of acetic anhydride to yield a partial melt when heated to the racemizing temperature.

14. The process of claim 1 wherein the composition to be racemized is a melt, which comprises heating the said melt to a temperature of between 5–10° C. over the melting temperature of the appropriate N-acetyl-D(L)-α-amino carboxylic acid or the pertaining salt thereof, whichever temperature is higher.

15. The process of claim 1 which comprises the step of taking up the composition resulting from the racemizing heating step, in water.

16. The process of claim 1 wherein the N-acetyl-D(L)-α-amino carboxylic acid to be racemized is selected from the group consisting of N-acetyl-D(L)-methionine, -valine, -phenylalanine and -norvaline.

17. The process of claim 1 wherein the N-acetyl-D(L)-α-amino carboxylic acid to be racemized is N-acetyl-D(L)-methionine.

18. The process of claim 1, which comprises the steps of treating N-acetyl-D(L)-methionine with sodium hydroxide solution to a pH value of 4–8, evaporating said solution to a melt, efficiently mixing said melt with from about 2 to about 6 wt. % of acetic anhydride, heating to 110–180° C. and after a reaction time of 2–30 minutes, taking up the resultant product in water.

19. The process of claim 18, which comprises the step of heating at 150–160° C.

20. The process of claim 18, which comprises the step of heating for 10–15 minutes.

21. The process in accordance with claim 20, comprising the steps of acetylating D,L-methionine with acetic acid/acetic anhydride, enzymatically splitting the thus obtained N-acetyl-D,L-methionine racemate, separating L-methionine under retention of a mother liquor containing unreacted N-acetyl-D(L)-Methionine, racemizing said mother liquor and recycling said racemized solution to the enzymatic racemate splitting.

* * * * *